(12) United States Patent
Miyama et al.

(10) Patent No.: US 8,475,382 B2
(45) Date of Patent: Jul. 2, 2013

(54) ULTRASOUND DIAGNOSTIC APPARATUS AND METHOD FOR TRACING MOVEMENT OF TISSUE

(75) Inventors: Koji Miyama, Tokyo (JP); Masafumi Ogasawara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 69 days.

(21) Appl. No.: 13/283,374

(22) Filed: Oct. 27, 2011

(65) Prior Publication Data

US 2012/0108971 A1    May 3, 2012

(30) Foreign Application Priority Data

Oct. 27, 2010    (JP) ................................. 2010-241316

(51) Int. Cl.
*A61B 8/00*    (2006.01)
(52) U.S. Cl.
USPC .......................................... 600/454; 600/437
(58) Field of Classification Search
USPC ........................... 600/437–469; 382/128–132
See application file for complete search history.

(56) References Cited

U.S. PATENT DOCUMENTS

| 5,622,174 | A  | 4/1997  | Yanazaki        |
| 5,860,931 | A  | 1/1999  | Chandler        |
| 6,258,031 | B1 | 7/2001  | Sunagawa et al. |
| 6,447,453 | B1 | 9/2002  | Roundhill et al.|
| 6,638,221 | B2 | 10/2003 | Abe et al.      |
| 6,770,034 | B2 | 8/2004  | Sunagawa et al. |
| 6,884,216 | B2 | 4/2005  | Abe et al.      |
| 7,022,077 | B2 | 4/2006  | Mourad et al.   |
| 7,455,640 | B2 | 11/2008 | Suzuki et al.   |
| 7,575,551 | B2 | 8/2009  | Watanabe et al. |
| 7,583,828 | B2 | 9/2009  | Hall et al.     |
| 7,815,574 | B2 | 10/2010 | Mourad et al.   |
| 8,167,802 | B2 | 5/2012  | Baba et al.     |
| 2002/0072672 | A1 | 6/2002 | Roundhill et al.|
| 2003/0009101 | A1 | 1/2003 | Sunagawa et al. |

(Continued)

FOREIGN PATENT DOCUMENTS

| JP | 06259560 | 9/1994 |
| JP | 11197152 | 7/1999 |

(Continued)

OTHER PUBLICATIONS

Japanese Office Action, Application No. 2010-241316; dated Oct. 1, 2012; pp. 3.

(Continued)

*Primary Examiner* — Sanjay Cattungal
(74) *Attorney, Agent, or Firm* — Armstrong Teasdale LLP

(57) ABSTRACT

An ultrasound diagnostic apparatus includes a transmitting and receiving unit that transmits an ultrasound wave to a target object and receives the ultrasound wave as ultrasound data reflected from the target object including a long axis direction blood vessel. An image generation unit generates an ultrasound image as a sectional image of the blood vessel. A region of interest (ROI) setting unit sets a first ROI on a vertical straight line at a right angle to the long axis direction and a second ROI on a wall of the blood vessel displayed at a designated time. A tracing unit traces movement of tissue in the target object corresponding to the first and second ROIs from the designated time to sequentially following thereafter by a gradient method using a spatial brightness gradient. A second memory unit stores information of the movement of the tissue for a predetermined duration.

20 Claims, 9 Drawing Sheets

U.S. PATENT DOCUMENTS

| | | |
|---|---|---|
| 2003/0083578 A1 | 5/2003 | Abe et al. |
| 2004/0059220 A1 | 3/2004 | Mourad et al. |
| 2004/0111028 A1 | 6/2004 | Abe et al. |
| 2006/0173292 A1 | 8/2006 | Baba et al. |
| 2006/0173309 A1 | 8/2006 | Suzuki et al. |
| 2007/0016031 A1 | 1/2007 | Mourad et al. |
| 2007/0032725 A1 | 2/2007 | Watanabe et al. |
| 2007/0055149 A1 | 3/2007 | Suzuki et al. |
| 2007/0167809 A1 | 7/2007 | Dala-Krishna |
| 2007/0213614 A1 | 9/2007 | Suzuki et al. |
| 2008/0095417 A1 | 4/2008 | Pedrizzetti et al. |
| 2009/0143675 A1 | 6/2009 | Suzuki et al. |
| 2009/0227867 A1 | 9/2009 | Suzuki et al. |
| 2010/0036248 A1 | 2/2010 | Chouno |
| 2010/0063391 A1 | 3/2010 | Kanai et al. |
| 2010/0198072 A1 | 8/2010 | Abe et al. |
| 2011/0054314 A1 | 3/2011 | Tanigawa et al. |
| 2011/0144495 A1 | 6/2011 | Wilkening et al. |

FOREIGN PATENT DOCUMENTS

| | | |
|---|---|---|
| JP | 2004077862 A | 3/2004 |
| JP | 2003250804 | 9/2009 |
| WO | 2006082966 A1 | 8/2006 |
| WO | 2008023618 A1 | 2/2008 |
| WO | 2009060732 A1 | 5/2009 |

OTHER PUBLICATIONS

Numata et al., Investigation on Interpolation Method of Ultrasonic RF Echoes for Measuring Longitudinal Displacement of Arterial Wall, Graduate School of Engineering, dated 2005, pp. 7.

Japanese Office Action, Application No. 2010-241316, dated Jan. 21, 2013, pp. 3.

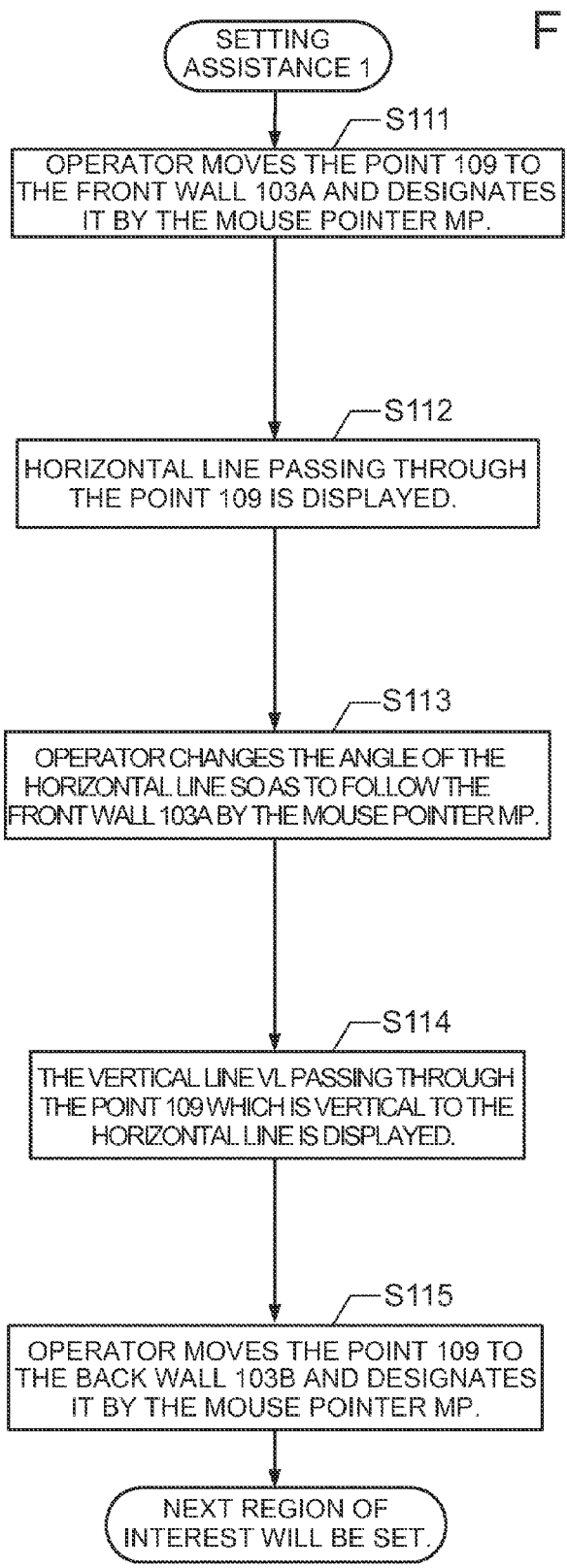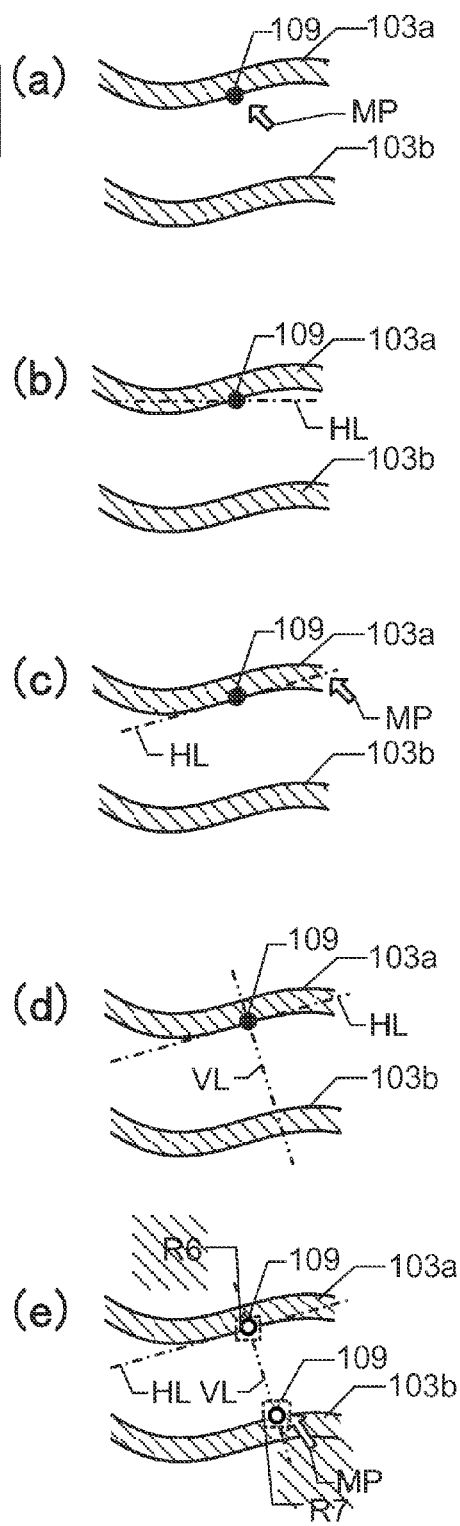
FIG. 5

FIG. 6
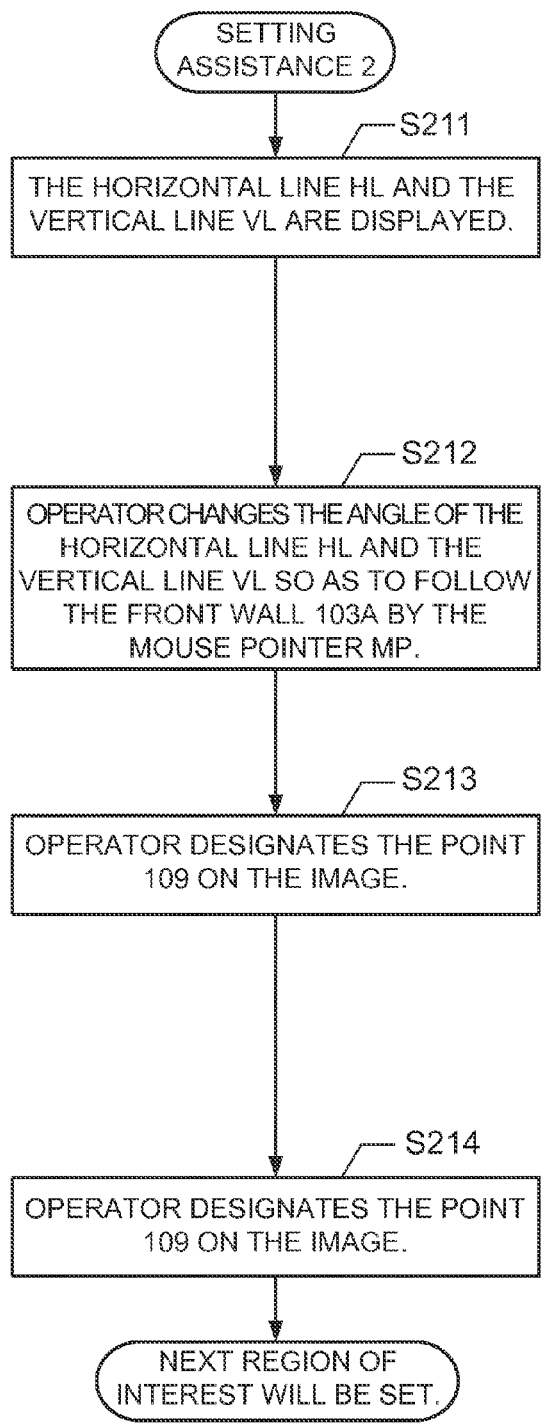
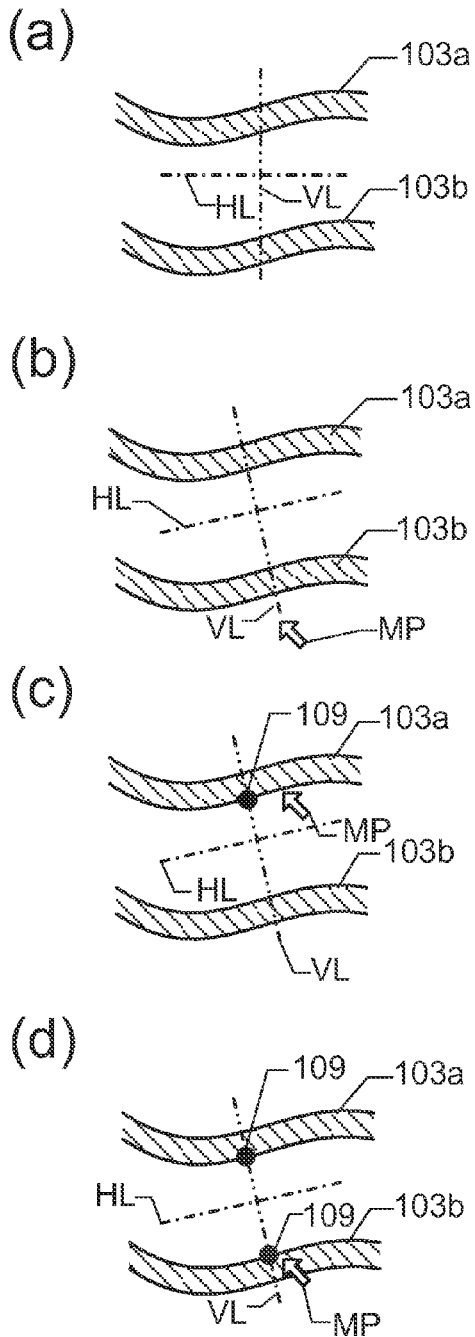

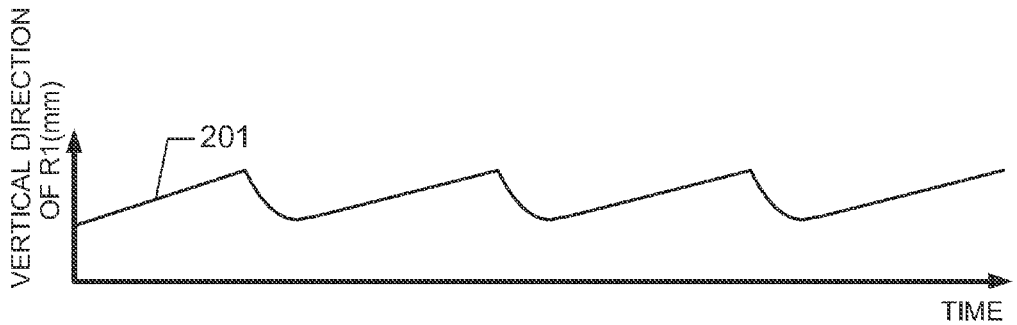
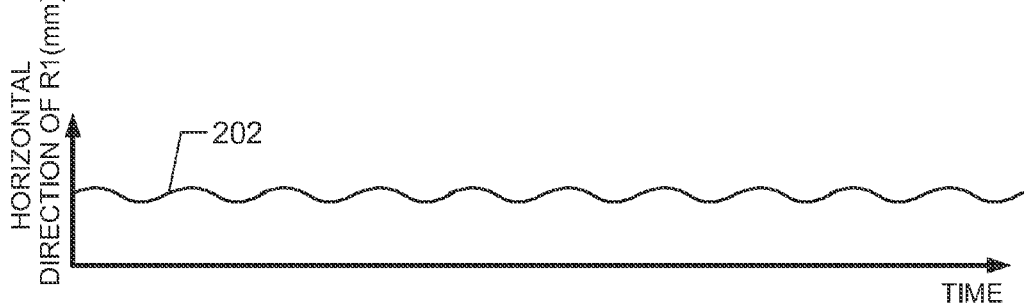
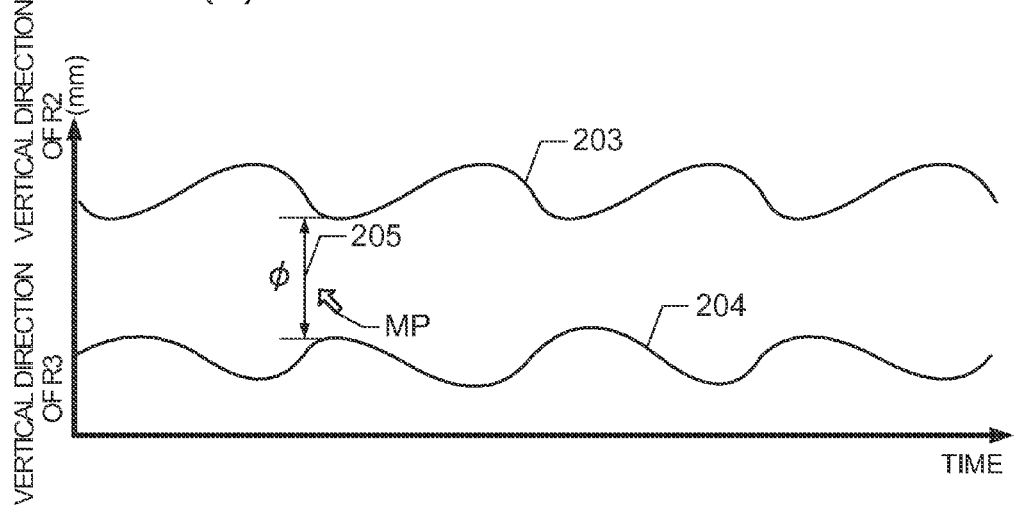

ULTRASOUND DIAGNOSTIC APPARATUS AND METHOD FOR TRACING MOVEMENT OF TISSUE

CROSS REFERENCE TO RELATED APPLICATIONS

This application claims the benefit of Japanese Patent Application No. 2010-241316 filed Oct. 27, 2010, which is hereby incorporated by reference in its entirety.

BACKGROUND OF THE INVENTION

The embodiments described herein relate to an ultrasound diagnostic apparatus for diagnosing blood vessel using ultrasound.

In recent years, number of patients diagnosed with circulatory condition, such as cerebral infarction and cardiac infarction, are on the rise. To prevent from such disease, it is important to detect a symptom of arteriosclerosis in its early stage and to improve a lifestyle.

To diagnose an arterial problem, Japanese unexamined publication 2002-238903A discloses an ultrasound diagnostic apparatus that measures the diameter of blood vessel using B (brightness)-mode image. Japanese unexamined publication 2002-238903A further discloses an ultrasound diagnostic apparatus for tracing the diameter of blood vessel and blood vessel wall in which an operator sets a mark for tracing in the B-mode image displayed in the monitor, and calculating a correlation of the brightness of pixel in a region of interest (ROI) that includes previously setup mark for tracing.

Unfortunately, the correlation of the brightness of pixel as described in Japanese unexamined publication 2002-238903A may vary the diameter of the blood vessel or the blood vessel wall depending on the image data processing. Also, by setting the region of interest (ROI) on the blood vessel, it is preferred that the inner diameter of the blood vessel or the thickness of the blood vessel wall is displayed.

It is desirable that the problems described previously are solved.

BRIEF DESCRIPTION OF THE INVENTION

A first aspect of the ultrasound diagnostic apparatus includes a transmitting and receiving unit for transmitting an ultrasound wave to a target object in sequence and for receiving the ultrasound wave as ultrasound data reflected from a certain region of the target object including a long axis direction blood vessel in sequence; a first memory unit for storing the received ultrasound data in sequence; an image generation unit for generating an ultrasound image as a sectional image of the long axis direction blood vessel based on the received ultrasound data; and a display unit for displaying the ultrasound image generated by the image generation unit.

The ultrasound diagnostic apparatus includes a region of interest setting unit for setting a first region of interest and a second region of interest on a vertical straight line at a right angle to the long axis direction blood vessel and on a wall of the blood vessel of the ultrasound image displayed in the display unit at a designated time, wherein the region of interest is generated by ultrasound data stored in the first memory unit; a tracing unit for tracing movement of tissue in the target object corresponding to the first region of interest and the second region of interest set in the ultrasound image at the designated time and sequentially following thereafter, by the gradient method using a spatial brightness gradient; and a second memory unit for storing information of the movement of the tissue for a predetermined duration based on the movement of tissue traced by the tracing unit.

In a second aspect of the ultrasound diagnostic apparatus, the display unit displays a traced result of the movement of the tissue on the vertical straight line and to a horizontal straight line normal to the vertical straight line, based on the information of the movement of the tissue stored in the second memory unit.

In a third aspect of the ultrasound diagnostic apparatus, the display unit displays the traced result of the distance between the tissues on the vertical straight line, based on the information of the movement of tissue stored in the second memory unit.

In a fourth aspect of the ultrasound diagnostic apparatus, the region of interest setting unit displays points for indications of the first region of interest and the second region of interest on the display unit.

In a fifth aspect of the ultrasound diagnostic apparatus, the region of interest setting unit displays a horizontal line in the long axis direction including the first region of interest on the display unit when the first region of interest is set on the vertical straight line, and displays a vertical line normal to the horizontal line including the first region of interest on the display unit when angle of the horizontal line is set. Then an operator can easily set the region of interest.

In a sixth aspect, the first region of interest includes a first inner wall of the blood vessel on the vertical straight line and the second region of interest includes a second inner wall of the blood vessel on the vertical straight line. The display unit displays a traced result of an inner diameter of the blood vessel identified by the first region of interest and the second region of interest.

In a seventh aspect, the first region of interest includes a first outer wall of the blood vessel on the vertical straight line and the second region of interest includes a second outer wall of the blood vessel on the vertical straight line. The display unit displays a traced result of an outer diameter of the blood vessel identified by the first region of interest and the second region of interest.

In an eight aspect, the region of interest setting unit sets a third region of interest and a fourth region of interest on the vertical straight line. The first region of interest includes a first inner wall of the blood vessel on the vertical straight line and the second region of interest includes a second inner wall of the blood vessel on the vertical straight line. The third region of interest includes a first outer wall of the blood vessel and the fourth region of interest includes a second outer wall of the blood vessel. The display unit displays a change in duration of a thickness of the blood vessel identified by the first and the second regions of interest and the third and the fourth regions of interest.

In a ninth aspect, the region of interest setting unit sets each region of interest corresponding to the first and the second regions of interest, which is in a different position from the first and the second regions of interest in the long axis direction.

In a tenth aspect, the display unit displays a traced result of an average distance based on the information of the movement of the tissue at the different position in long axis direction stored in the second memory unit. The average distance between the tissues of the target body on the vertical straight line is calculated at a plurality of different positions.

In an eleventh aspect, the region of interest setting unit sets a new region of interest on the horizontal straight line. The tracing unit traces movement of tissue in the target object corresponding to the region of interest on the horizontal straight line. The display unit displays the points, the first region of interest and the second region of interest when the first region of interest and the region of interest on the horizontal straight line are moved.

The ultrasound diagnostic apparatus described herein can trace a movement of a target object within the predetermined region, including a blood vessel, by using a gradient method and accurately measure the movement of tissue in the target object.

Further objects and advantages of the present invention will be apparent from the following description of the preferred embodiments of the invention as illustrated in the accompanying drawings.

BRIEF DESCRIPTION OF THE DRAWINGS

FIG. 5 shows the first example of setting the ROI with assistance from the region of interest setting unit 125.

FIG. 6 shows the second example of setting the ROI with assistance from the region of interest setting unit 125.

FIG. 8 (a) shows an example diagram of the traced result of the ROI (R1) to the vertical direction, displayed in the display unit 127.

FIG. 8 (b) shows an example diagram of the traced result of the ROI (R1) to the horizontal direction, displayed in the display unit 127.

FIG. 8 (c) shows an example diagram of the traced result of the ROI (R2) and the ROI (R3) to the vertical direction, displayed in the display unit 127.

FIG. 9 (b) is a graph 211 showing the thickness of the front wall 103a.

FIG. 9 (c) is a graph 212 showing the thickness of the front wall 103a, which is different from the ROI to the long axis direction in FIG. 9 (b).

FIG. 9 (d) is a graph 213 showing the thickness of the average blood vessel wall thickness of the front wall 103a.

DETAILED DESCRIPTION OF THE INVENTION

<Configuration of the Ultrasound Diagnostic Apparatus 100>

Figure 1:
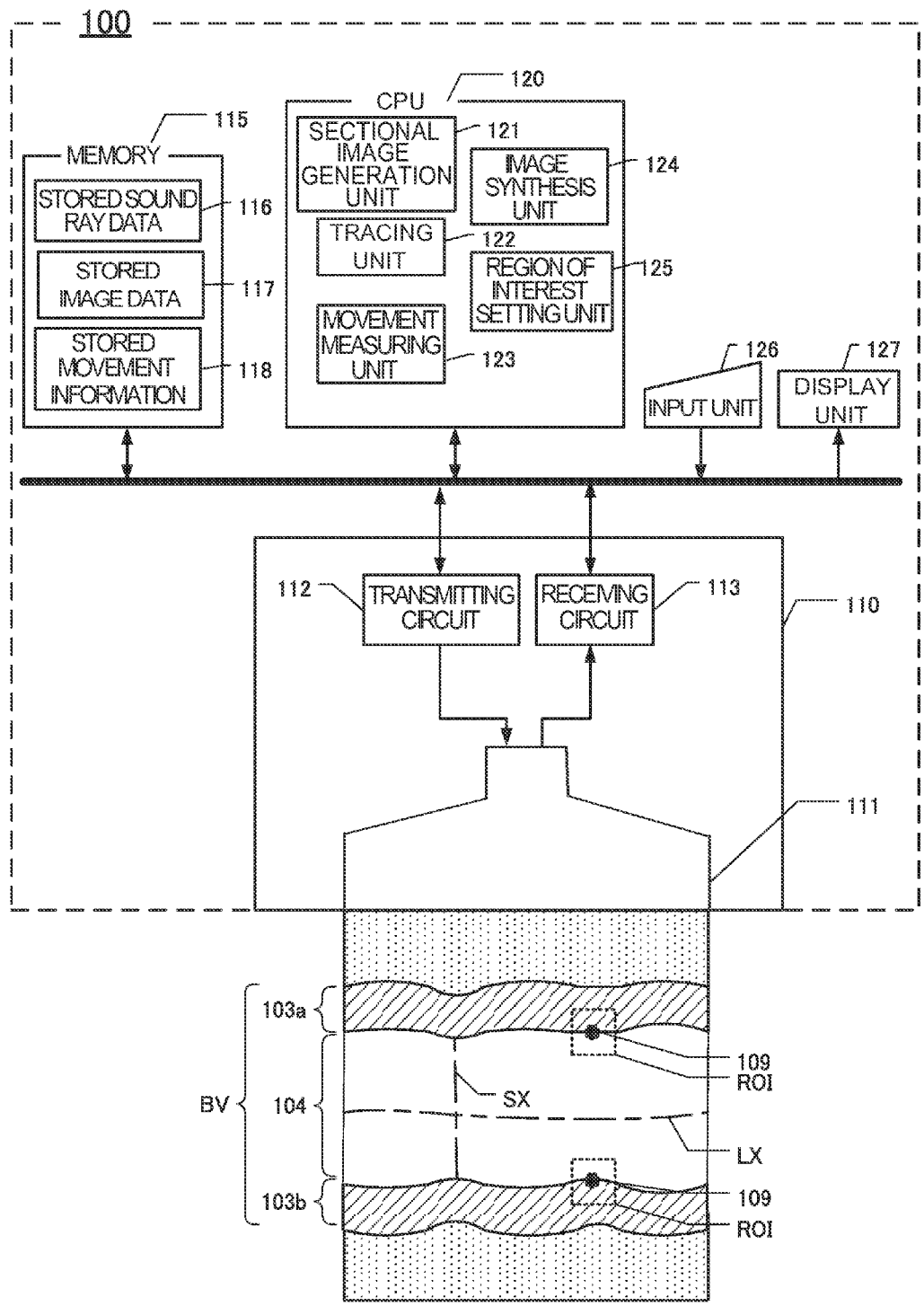
FIG. 1 is an overall diagram of an ultrasound diagnostic apparatus.

FIG. 1 is a block diagram showing the configuration of the ultrasound diagnostic apparatus 100. The ultrasound diagnostic apparatus 100 includes a transmitting and receiving unit 110 connected to a parallel bus, a memory 115, a CPU (central processing unit) 120, an input unit 126 for inputting through a mouse or a keyboard and display unit 127 having an LCD unit.

The transmitting and receiving unit 110 includes an ultrasound probe 111, a transmitting circuit 112 and a receiving circuit 113. The ultrasound probe 111 includes a plurality of ultrasound transducers in a 1-dimensional or a 2-dimensional transducer array. The ultrasound transducers transmit ultrasound waves based on applied driving signal to the target object, receive ultrasound echo reflected from the target object, and output a receiving signal.

The transmitting circuit 112 includes a plurality of channels, and generates a plurality of driving signals applied to each plurality of ultrasound transducers. The transmitting circuit 112 can adjust an amount of delay in the plurality of driving signals so that the ultrasound transmitted from a plurality of ultrasound transducers forms an ultrasound beam thereafter. Also, the transmitting circuit 112 can provide to the ultrasound probe 111a plurality of driving signals, set for transmitting an ultrasound transmitted from the plurality of ultrasound transducers all at once to the image region of the target object.

The receiving circuit 113 includes a plurality of channels, receives a plurality of analog receiving signals outputted from each plurality of ultrasound transducers and amplifies thereof, and converts to digital receiving signals. Moreover, based on a received delay pattern selected from the transmitting and receiving unit 110, the receiving circuit 113 applies each delay time to a plurality of receiving signals, and processes receiving focus by adding all of the receiving signals. Due to the receiving focus processing, the sound ray data with focused ultrasound echo is formed.

In this embodiment, the ultrasound probe 111 transmits ultrasound waves from the surface of the target object to a blood vessel BV inside the target object. Also, the ultrasound probe 111 receives an ultrasound echo from the target object, including the blood vessel. The transmitting and receiving unit 110 repeats the transmission of the ultrasound waves and reception of the ultrasound echo, for outputting the sound ray data in sequence. The sound ray data processes logarithm compression, gain adjustment or low-pass filter processing in the receiving circuit 113, and processes an attenuation correction according to a depth of the reflecting position of ultrasound. The processed sound ray data is sequentially stored in the memory 115 through the parallel bus.

The memory 115 has capacity for storing a plurality of frames of the sound ray data 116 or a sectional image data 117, generated by an image generation unit 121.

CPU 120 includes the image generation unit 121, the tracing unit 122, the movement measuring unit 123, the image synthesis unit 124 and the region of interest setting unit 125.

The image generation unit 121 includes an image data generation function for inputting the sound ray data and generating sectional image data in B-mode. The image generation unit 121 converts the B-mode sectional image data into the sectional image data that complies to the scan method of a normal television signal, performs image processing necessary for gradation process and transmits to an image synthesis unit 124 or a display unit 127, and sequentially stores the sectional image data etc. into the memory 115.

Also, in live mode, the image generation unit 121 converts the directly supplied sound ray data into the sectional image data according to a scanning method, and in freeze mode, the image generation unit 121 converts the sectional image data 117 stored in the memory 115, into the sectional image data according to the scanning method. Moreover, during the freeze mode, if the memory 115 is storing the sound ray data 116 instead of the sectional image data 117, the image generation unit 121 generates the B-mode sectional image data.

The region of interest setting unit 125 displays the intersection point 109 for indicating the region of interest (ROI) to the ultrasound image using the input unit 126, such as a mouse. According to the movement of the mouse operated by an operator, the point 109 moves within the display unit 127. Then, the region of interest setting unit 125 sets the ROI that is the surrounded region including the indicated point 109, based on the signal from the point 109 indicated by the operator, to the ultrasound image displayed by using the image data supplied from the receiving circuit 113. The region of interest setting unit 125 automatically sets the size of the ROI. The region of interest setting unit 125 extracts the image data at the ROI. Once the ROI is set, the region of interest setting unit 125 extracts the sectional image data of the ROI corresponding to the sectional image data 117, which is stored in the memory 115 (or the sound ray data 116 stored in the memory 115). The sectional image data extracted according to the ROI set by the region of interest setting unit 125 is supplied to the tracing unit 122.

Although, the point 109 indicated with a black circle and the ROI indicated in rectangle is displayed in FIG. 1 of the diagram of the blood vessel in the long axis direction in the target object, the ROI does not always need to be indicated in the display unit 127. Also, if the traced result informs that the blood vessel is moving as a whole from the tracing unit 122, as explained below, the display unit 127 can display the point 109 and the ROI to trace the movement of the blood vessel as a whole.

The tracing unit 122 traces which vector direction the ROI is moving to, from the predetermined time. To trace the ROI, a method of calculating the velocity field of the motion object in the moving image (optical flow) is used. There are many methods in an optical flow. According to an experiment, a gradient method was suitable for tracing a blood vessel wall. The gradient method is suitable for tracing minute movements and especially for tracing minute movements of the blood vessel wall. The result of the tracing unit 122 tracing the ROI is transmitted to the image synthesis unit 124, the movement measuring unit 123 and the memory 115.

Also, the tracing unit 122 traces the movement of a whole blood vessel in the long axis direction or rotation. An example case of the blood vessel moving or rotating as a whole would be losing contact between the ultrasound probe 111 and the target object.

The movement measuring unit 123 measures the movement distance of tissue at a predetermined time based on the movement of tissue in the ROI traced by the tracing unit 122. Thus, the movement measuring unit 123 can calculate the change in the diameter of the blood vessel or the elasticity of the blood vessel based on the movement distance of tissue. The traced result measured by the movement measuring unit 123 is transmitted to the image synthesis unit 124, the memory 115 and the display unit 127. The traced result transmitted to the memory 115 is stored as movement information 118. The traced result transmitted to the display unit 127 is displayed in real-time as the total amount of movement of tissue inside the ROI.

The image synthesis unit 124 synthesizes the sectional image data supplied from the image generation unit 121, the movement information 118 traced by the tracing unit 122 and the traced result measured in the movement measurement unit 123, and synthesizes two images therewith. Image synthesis unit 124 can retrieve the sound ray data 116 or sectional image data 117, stored in the memory 115, on a necessary basis.

A diagram of a blood vessel in the long axis direction inside the target object as indicated in FIG. 1 is explained below.

Blood vessel includes a blood vessel wall 103, which surrounds a blood flow region 104. Blood vessel wall 103 includes a front wall 103a, which is a wall closer to the ultrasound probe 111, and a back wall 103b, which is a wall farther from the ultrasound probe 111. In FIG. 1, the ROI set by the region of interest setting unit 125 is positioned on the front wall 103a and the back wall 103b. The long axis direction LX refers to the blood vessel extending in the longitudinal direction at the center of the blood flow region 104, and the short axis direction SX refers to the cross-section of the blood vessel (vertical straight line normal to the long axis direction LX).

<Method for Measuring Blood Vessel>

Figure 2:
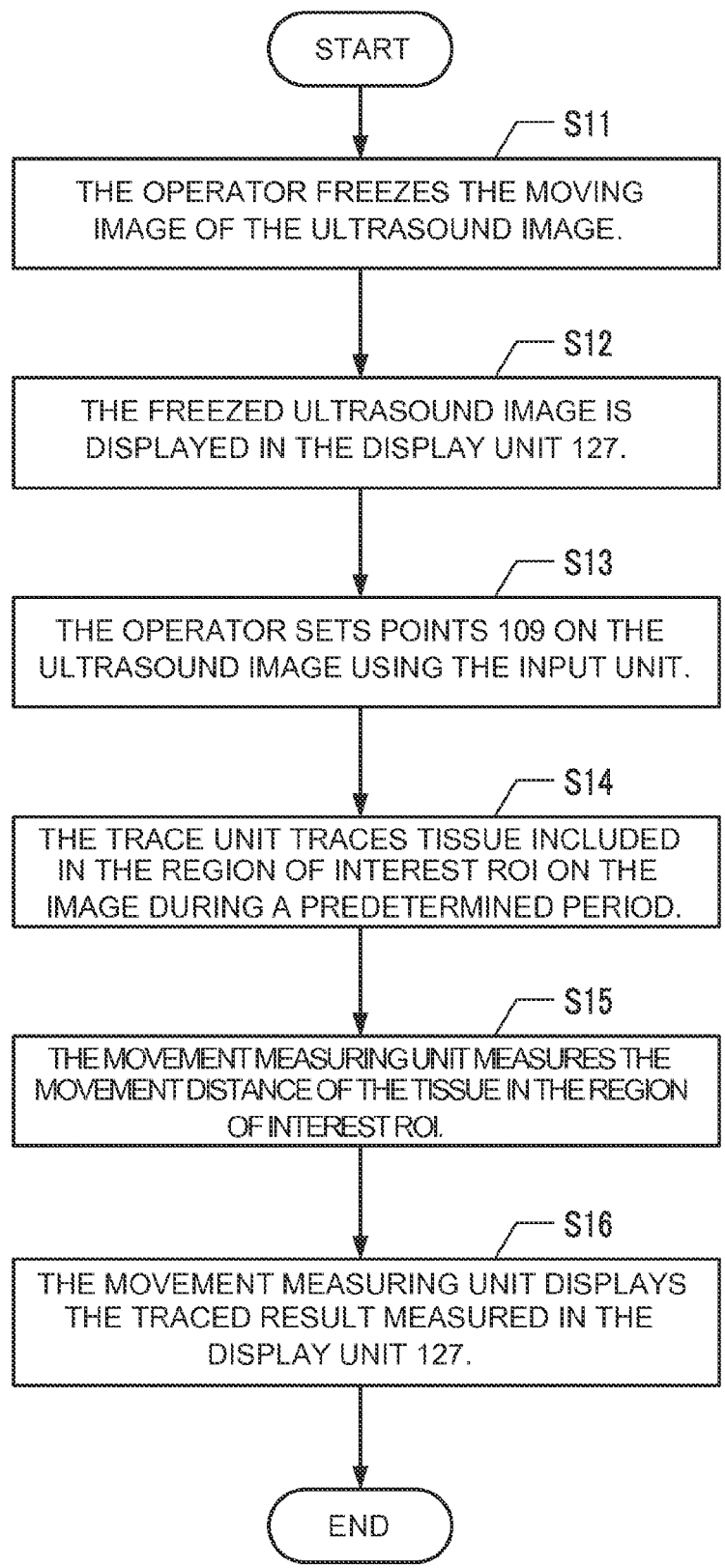
FIG. 2 is a flowchart showing the method of measuring blood vessel in accordance with a present embodiment.

FIG. 2 is a flow chart showing the method for measuring the blood vessel.

In step S11, the operator confirms that the moving image of the ultrasound image is stably obtained, and presses a freeze button (not described on figure).

In step S12, when the freeze button is pressed, the sound ray data 116 or the sectional image data 117 acquired during a few seconds after pressing the freeze button is stored in the memory 115, and the ultrasound image stored in the first frame is displayed in the display unit 127. The sound ray data 116 or the sectional image data 117 acquired a few seconds after pressing the freeze button can be stored in the memory 115 as well.

In step S13, the operator indicates the point 109 in the ultrasound image displayed on the first frame displayed in the display unit 127 by using the input unit 126 connected by a parallel bus, such as a mouse. The region of interest setting unit 125 sets the ROI to the surrounding region, including the point 109. The operator can easily set the ROI to the blood vessel inside the target object, which is displayed in the display unit 127. In this embodiment, at least two or more ROIs should be set.

In step S14, the tracing unit 122 traces the movement of tissue, which includes at least two points of the ROI, using frames of ultrasound images between the initial frame of the ultrasound image and the frame of the ultrasound image after the predetermined duration. The ROI is traced using the gradient method.

In step S15, the movement measuring unit 123 traces, for example, the movement of tissue included at two points of the ROI. For example, if the inner wall of the front wall 103a and the inner wall of the back wall 103b are the two points of the ROIs, the movement measuring unit 123 is able to understand how the inner diameter of the blood vessel is changing, in comparison to the ultrasound image of the first frame.

In step S16, the display unit 127 displays the traced result, measured by the movement measuring unit 123, in a graph for example. The display unit 127 is able to display a graph adjacent to the displayed ultrasound image, or display a graph on a separate window.

<Tracing the ROI by Gradient Method>

An optical flow method for the tracing unit 122 tracing the movement of tissue in the ROI, at step S14, is explained below. In the optical flow method, a characteristic matching method, a method for matching the characteristic of images and calculating the movement, and a gradient method, a method for calculating the movement by calculating the gradient of the contrasting density (brightness) of an image for comparing the contrasting density of the image, is used. An experiment using both the characteristic matching method and the gradient method was performed on the ultrasound image including the blood vessel displayed in the B-mode. As a result, less difference in tracing was found in the gradient method. Thereby the gradient method is explained below.

Figure 3:
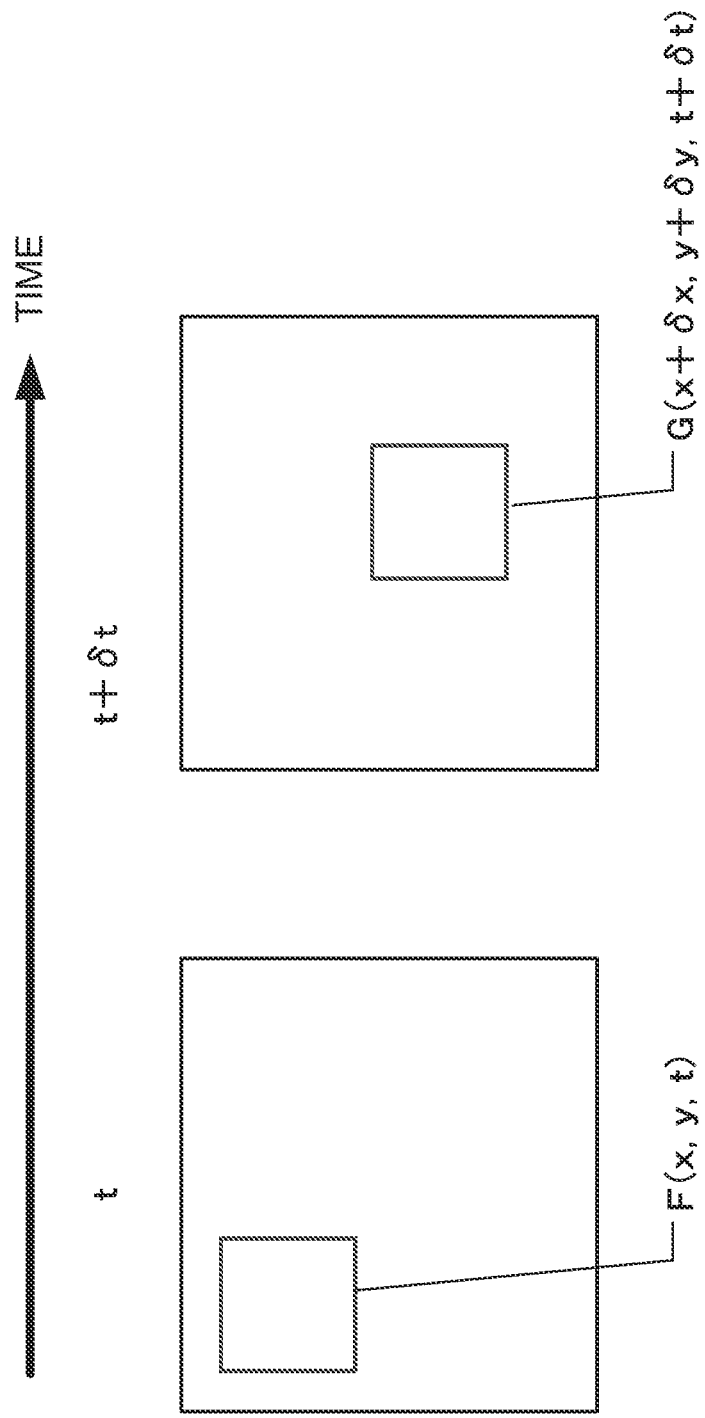
FIG. 3 is a diagram explaining the brightness gradient of the grayscale image.

As shown in FIG. 3, the contrasting density image F (p, t) includes a gradient of contrasting density (brightness gradient). The gradient method traces the movement of tissue included in the ROI by using the gradient of contrast.

As shown in FIG. 3, an image of contrasting density image "F" at time "t" (p, t) moved with even contrasting density after a minute duration (δ, t), is calculated as contrasting density image G (p+δp, t+δt). The distance of movement is calculated using the following equation:

$$h_0 = 0, \tag{Eq. 1}$$

$$h_{k+1} = h_k + \frac{\sum w(p)F'(p+h_k)[G(p) - F(p+h_k)]}{\sum w(p)F'(p+h_k)^2}$$

The movement distance (vector) of tissue in the ROI is calculated by doing the iterative operation of equation 1.

In equation 1, "h" represents the distance of approximate movement, w (p) represents the weight coefficient, F (p) represents the contrasting density image before the movement, and F' (p) represents the first derivation.

The gradient method is suitable for tracing minute movements such as movement of the blood vessel wall due to the heartbeat. By tracing the movement of tissue included in the ROI using the gradient method, the minute movement of the blood vessel wall due to the heartbeat can be accurately traced.

<Setting the ROI>

Figure 4:
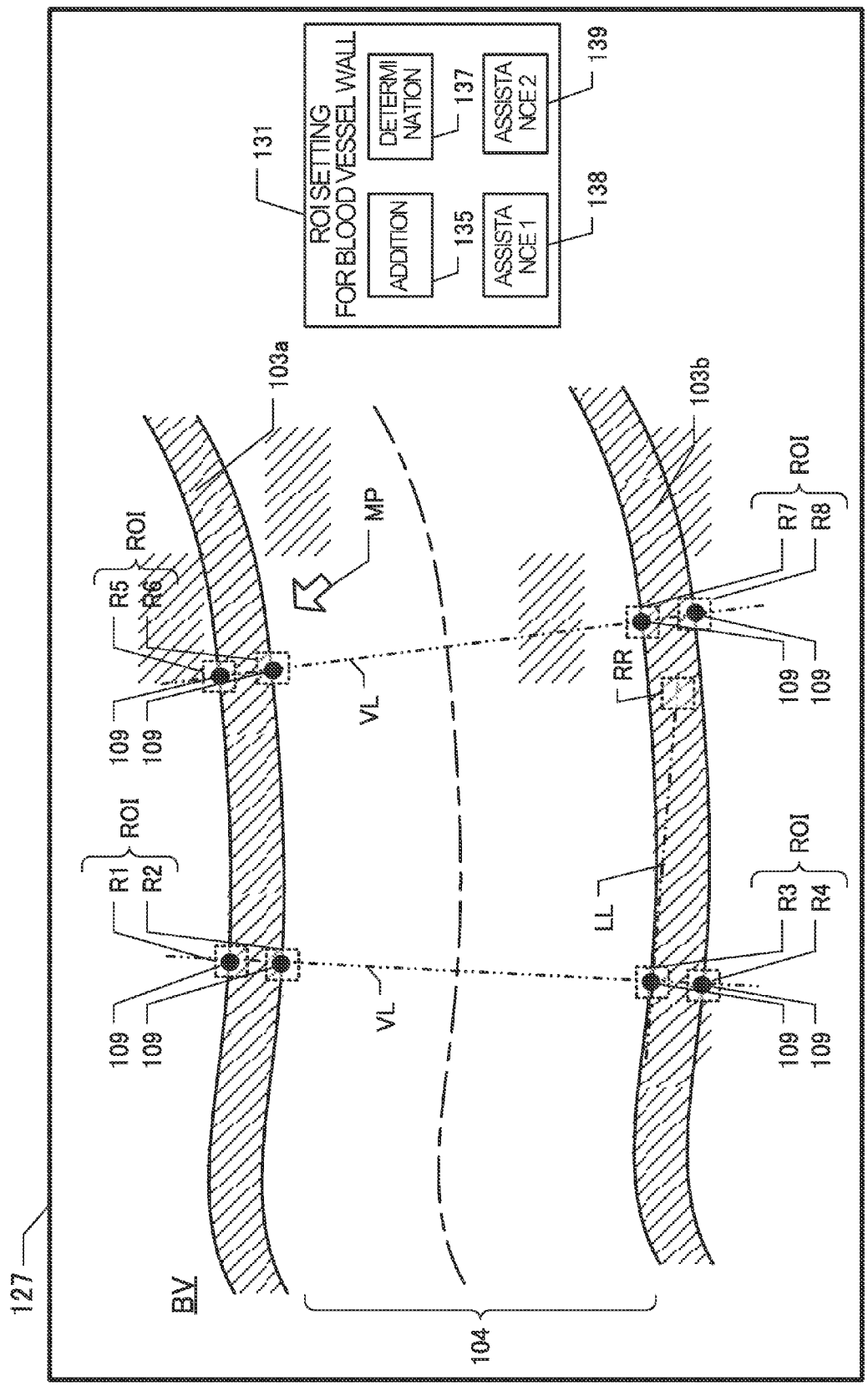
FIG. 4 is a diagram showing the setup region of interest (ROI) in the blood vessel (BV).

FIG. 4 is a diagram showing the ROI in the blood vessel extending in the long axis direction, as displayed in the display unit 127, which was set by an operator. This is the same method as setting the ROI in the step S13 of FIG. 2.

An operator checks the ultrasound image of the initial frame displayed in the display unit 127. Then, the operator checks whether the blood vessel extending in the long axis direction is a sectional image that can easily set the ROI, and if the sectional image is an image that can easily set the ROI, the operator clicks the ROI setting button (not described on figure) through the input unit 126, using the mouse pointer. The region of interest setting unit 125 (refer to FIG. 1) displays the ROI setting window 131 for the blood vessel wall, on the display unit 127.

The ROI setting window 131 for the blood vessel wall includes an adding button 135, a determination button 137, a first assistance button 138 and a second assistance button 139.

When the adding button 135 is selected with the mouse pointer MP, the point 109 of predetermined size is displayed in the display unit 127. When the adding button 135 is selected a plurality of times, a plurality of points 109 are displayed in the display unit 127. In FIG. 4, eight of the points 109 are displayed in the display unit 127.

For each point 109 displayed in the display unit 127, the operator can move displayed points to an arbitrary position one-by-one using the mouse pointer and can designate the position. In FIG. 4, the operator designates points 109 on four positions in the long axis direction (short axis direction) of the blood vessel. Based on the designated point 109, the region of interest setting unit 125 sets the ROIs (R1 and R2) on the outer wall and the inner wall of the front wall 103a and sets ROIs R3 and R4 on the outer wall and the inner wall of the front wall 103b. Also, the operator is designating the point 109 at four positions farther away from the ROIs (R1 through R4) in the long axis direction. Based on the designated points 109, the region of interest setting unit 125 sets the ROIs R5 and R6 on the outer wall and the inner wall of the front wall 103a, and sets the ROIs R7 and R8 on the outer wall and the inner wall of the back wall 103b. Once the operator completes setting all of the regions of interest, the operator selects the determination button 137. Also, the operator can display the horizontal line or the vertical line for assisting the setting of the ROI, by selecting the first assistance button 138 or the second assistance button 139. In FIG. 4, the ROI is displayed in the display unit 127 using dotted lines. However, the point 109 can only be displayed without displaying the ROI.

When at least one point 109 is designated, the region of interest setting unit 125 sets a new region of interest RR along the horizontal straight line LL extending in the horizontal direction from the point 109. The horizontal straight line LL and the region of interest RR do not need to be displayed in the display unit 127. In FIG. 4, the horizontal straight line LL and the region of interest RR along the horizontal straight line LL are displayed according to the point 109 on the ROI R3. The tracing unit 122 traces the movement of the region of interest R3 and the newly set region of interest RR. For example, if the ROI R3 and the region of interest RR are moving with the same size and in the same direction, the tracing unit 122 is able to determine that the blood vessel is moving as a whole. When the tracing unit 122 transmits to the region of interest setting unit 125 and the display unit 127 that the blood vessel is moving as a whole, the region of interest setting unit 125 traces the movement as a whole, to all points 109 and the ROI relating to the points 109. Thus, even if the blood vessel displaces as a whole, the point 109 and the ROI relating to the point 109 traces the position originally designated or set. Finally, the movement unit 127 traces the vertical straight line VL extending from the point 109 and the ROI relating to the point 109.

<Assisting the Setting of the ROI: First Example>

FIG. 5 is the first example of setting the ROI with assistance from the region of interest setting unit 125 (refer to FIG. 1). The flowchart on the left side corresponds to the drawing of conditions thereof, indicated on the right side. In the first example of FIG. 5, the ROI is set on the inner wall of the front wall 103a and the inner wall of the back wall 103b. Therefore, R6 and R7 of the ROI, set in the FIG. 4, are displayed.

The operator selects the first assistance button 138 (refer to FIG. 4), and then selects the adding button 135. The point 109 is displayed in the display unit 127.

In the step S111, the operator indicates the point 109 on the inner wall of the front wall 103a, which the operator wants to observe, by moving the mouse pointer. Then, the operator selects the determination button 137.

In step S112, the region of interest setting unit 125 displays the horizontal line HL, which passes through the point 109 and has a predetermined length with the point 109 as a center. The horizontal line HL is parallel to the horizontal line 127, and is displayed as a tangent line to the inner wall of the front wall 103a in the long axis direction.

In step S113, the operator changes the angle of the horizontal line HL using the mouse pointer MP. Once the angle of the horizontal line HL is changed in such a way that it extends vertically to the front wall 103a, the operator selects the determination button 137.

In step S114, the region of interest setting unit 125 displays the vertical line VL, which passes through the point 109 and is vertical to the horizontal line HL with the angle changed.

In step S115, the operator selects the adding button 135, displays the point 109 on the display unit 127, and indicates the point 109 on the inner wall of the back wall 103b that the operator wants to observe by moving the mouse pointer MP. At this point, two regions of interests R6, R7 based on two points of the point 109 is set. In order to set three or more regions of interest, the operator continues the operation. If it is not necessary to set more than two regions of interest, the operator selects the determination button 137.

If the inner wall of the front wall 103a is bent due to the heartbeat, it is difficult to set another point 109 in the vertical direction (to the short axis direction) of the point 109. Therefore, as mentioned above, the horizontal line HL of the predetermined length with the point 109 as a center is to be displayed, and after changing the angle of the horizontal line HL, the vertical line VL is to be displayed. This sets the ROI R2 and the ROI R3 accurately in the vertical direction, therefore the diameter of the blood vessel can be accurately verified.

In the vertical line (VL) indicated in FIG. 4, the ROIs R1-R4 are set in the vertical direction accurately. Thus, the thickness of the front wall 103a of the blood vessel can be accurately verified based on the ROI R1 or the ROI R2, or the thickness of the back wall 103b can be accurately verified based on the ROI R3 or the ROI R4.

<Assisting the Setting of the ROI: Second Example>

FIG. 6 is the second example of setting the ROI with assistance from the region of interest setting unit 125 (refer to FIG. 1). As similar to the first example, the ROI is to be set onto the inner wall of the front wall 103a and the inner wall of the back wall 103b.

The operator selects the second assistance button 139 (refer to FIG. 4).

In step S211, the region of interest setting unit 125 displays the horizontal line HL and the vertical line VL.

In step S212, the operator changes the angle of the horizontal line HL and the vertical line VL using the mouse pointer, and moves the vertical line VL to the position to be observed. By rotating and moving a part of the horizontal line and the vertical line using the mouse pointer, the horizontal line HL and the vertical line VL rotate and move as a whole, while maintaining the right angle.

In step S213, when the operator selects the adding button 135, the region of interest setting unit 125 displays the point 109 on the display unit 127. Then the operator moves the point 109 along the inner wall of the front wall 103a on the vertical line VL that the operator wants to observe using the mouse pointer MP.

In step S214, when the operator selects the adding button 135, the point 109 is displayed on the display unit 127. Then, the operator moves the point 109 to the inner wall of the back wall 103b on the vertical line that the operator wants to observe by moving the mouse pointer MP. In order to set three or more ROIs, the operator continues the operation. The operator selects the determination button 137, if it is not necessary to set more than two ROIs.

Also, in FIG. 5 or FIG. 6, the horizontal line HL or the vertical line VL can be drawn directly on the screen of the display unit 127, which the horizontal line HL or the vertical line VL is displayed, by selecting the first assistance button 138 or the second assistance button 139.

<Tracing Information of the ROI>

Figure 7:
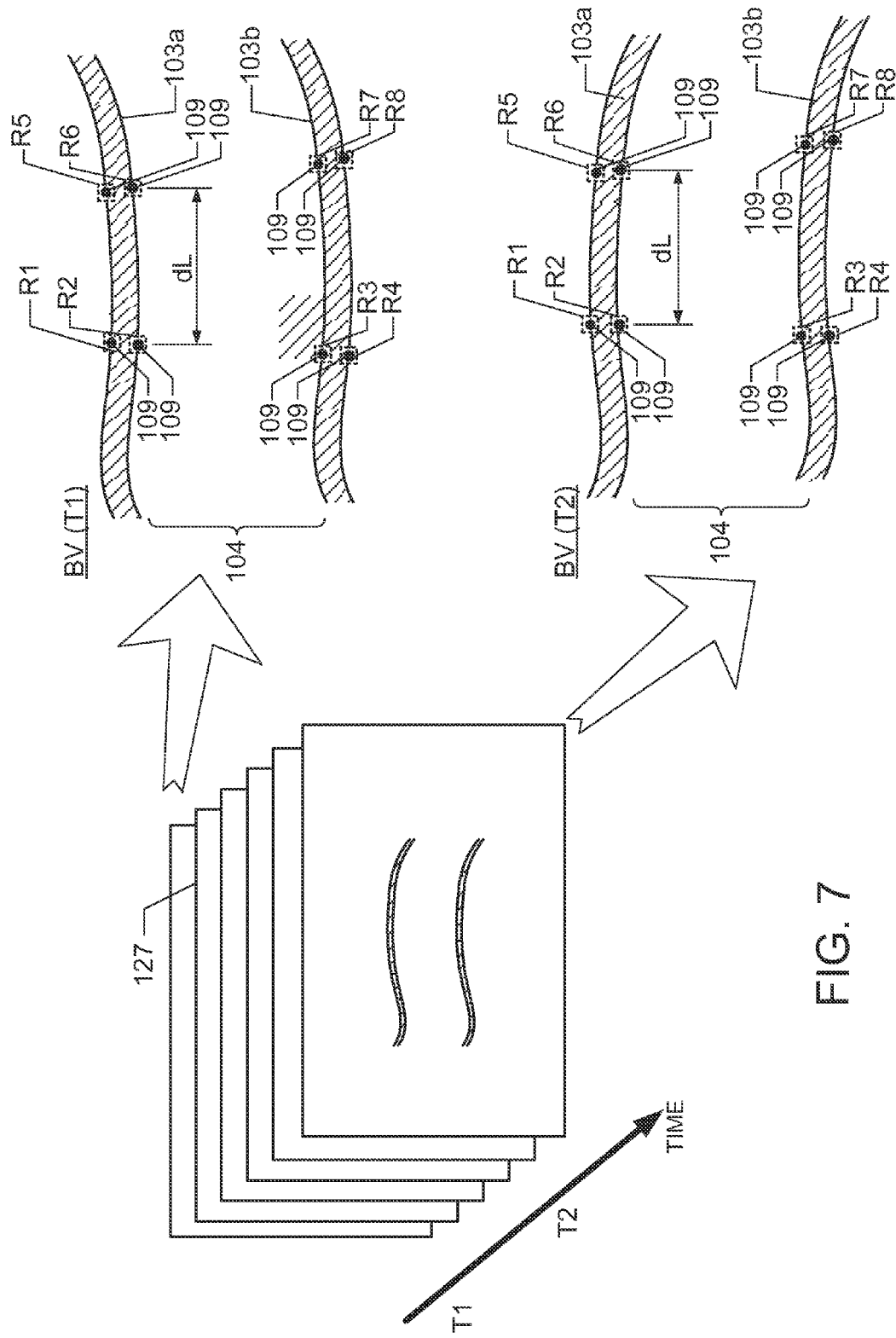
FIG. 7 shows the sequence of ultrasound image displayed in the display unit 127.

FIG. 7 shows the sequence of ultrasound image displayed in the display unit 127 after the point 109 is indicated and the ROI is set. The left side of FIG. 7 shows a plurality of frames of the ultrasound image between the predetermined time T1 and the predetermined time T2 being displayed, and the right side of FIG. 7 includes abstracts from the frame sequence taken from the ultrasound image at time T1 and the ultrasound image at time T2.

The cross-sectional shape of the blood vessel in the long axis direction changes between time T1 and time T2 due to the heartbeat. Tissue indicated with the ROIs R1-R8 moves in the horizontal direction (long axis direction) and the vertical direction (short axis direction) respectively. In this embodiment, eight ROIs are set, and by selecting one ROI R1, the movement measuring unit 123 can measure the amount of the movement of the ROI R1 in the vertical direction and the horizontal direction. Also, by selecting at least two ROIs among the eight ROIs, the movement measuring unit 123 can measure the movement information of these two ROIs.

FIGS. 8(a), 8(b), 8(c), 9(a), 9(b), 9(c), and 9(d) are examples of displaying the traced result measured by the movement measuring unit 123 at step S16 of FIG. 2, in a graph. These graphs are displayed based on the movement of the ROIs R1-R8 indicated in FIG. 7.

FIG. 8(a)-(c) are graphs indicating the traced result of the ROI of the blood vessel.

FIG. 8(a) is an example of the movement measuring unit 123 displaying the traced result of the ROI R1 in the vertical direction on the display unit 127. The vertical axis represents the position (in mm) and the horizontal axis represents time. The graph 201, displaying the traced result of the ROI R1 in the vertical direction, indicates that the outer wall of the front wall 103a, which also is the ROI R1, is largely moving due to the heartbeat.

FIG. 8(b) is an example of the movement measuring unit 123 displaying the traced result of the ROI R1 in the horizontal direction on the display unit 127. The graph 202, displaying the horizontal direction of the ROI R1, indicates that the outer wall of the front wall 103b is moving in the horizontal direction due to the heartbeat, and the amount of movement is smaller in comparison to the movement in the vertical direction, as shown in FIG. 8(a).

FIG. 8(c) is an example of the movement measuring unit 123 displaying the traced result of the ROI R2 and the ROI R3 in the vertical direction, on the display unit 127. ROI R2 is the inner wall of the front wall 103a, and the ROI R3 is the inner wall of the back wall 103b. The graph 203, displaying the vertical direction of the ROI R2, indicates that the inner wall of the front wall 103a is moving due to the heartbeat, and the graph 204, displaying the vertical direction of the ROI R3, indicates that the inner wall of the back wall 103b is moving due to the heartbeat. Also, since the ROI R2 and the ROI R3 are placed on the vertical direction (short axis direction) to the blood vessel. The difference between the graph 203 and the graph 204 being equals to the inner diameter of the blood vessel. By displaying the inner diameter index 205 and the operator moving the inner diameter index 205 using the mouse pointer, it is possible for the movement measuring unit 123 to display the inner diameter of the blood vessel for an arbitrary time.

FIG. 9(a)-(d) are graphs displaying the thickness of blood vessel wall, which is one of the traced results.

Figure 9:
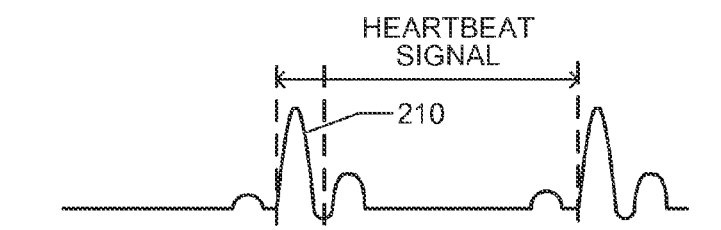
FIG. 9 (a) is a graph 210 for the heartbeat signal.
Figure 9:
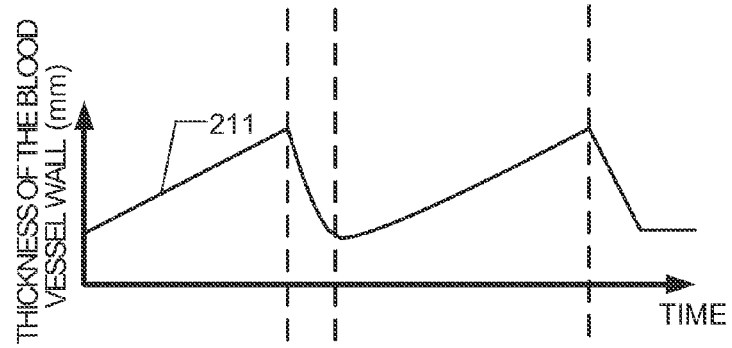
Figure 9:
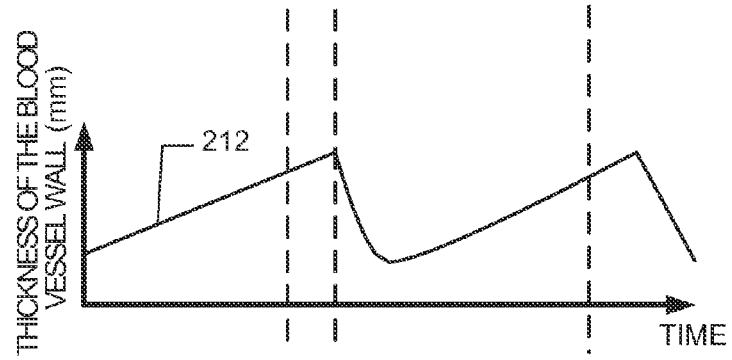
Figure 9:
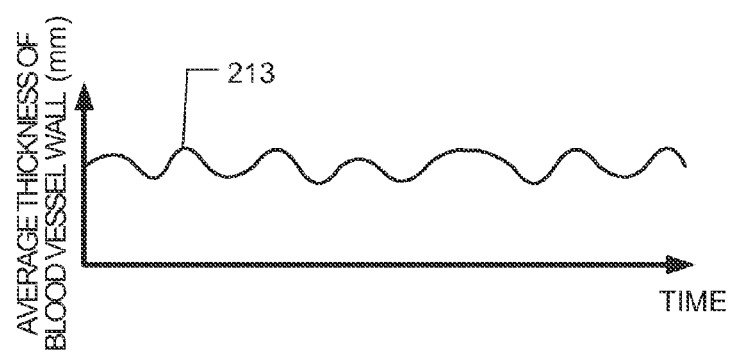

FIG. 9(a) is the graph 210 of the heartbeat signal. The heartbeat signal is displayed by placing the sensor (not described on figure) on the target object thereof.

FIG. 9(b) is an example of the movement measuring unit 123 displaying the difference between the ROI R1 and the ROI R2 in the vertical direction, which corresponds to the thickness of the front wall 103a, on the display unit 127 in the graph 211. The graph 211, which is the thickness of the front wall 103a, is displayed by synchronizing to the graph 210 of the heartbeat signal.

FIG. 9(c) is an example of the movement measuring unit 123 displaying the difference between the ROI R5 the ROI R6 in the vertical direction, which corresponds to the thickness of the front wall 103a, on in the display unit 127. The graph 212, which is the thickness of the front wall 103a, is displayed by synchronizing to the graph 210 of the heartbeat signal. As displayed in FIG. 7, the ROI R2 and the ROI R6 are positioned at the distance dL away from the long axis direction. Thus, the thickness of the blood vessel due to the heartbeat is different. By comparing the graph 211 and the graph 212, the change in time between the graph 211 and the graph 212 can be calculated. Therefore, the pulse wave velocity (PWV), a parameter for arteriosclerosis, can be calculated as well.

FIG. 9(d) is an example of the movement measuring unit 127 displaying the graph 213, which indicates the movement measuring unit 123 displaying the average thickness of blood vessel wall of the front wall 103a. In FIG. 7, the movement measuring unit 123 measured the thickness of the front wall 103a with the ROI (R1) and the ROI (R2), and the thickness of the front wall 103a with the ROI (R5) and the ROI (R6). The graph 213 of the average blood vessel wall thickness is obtained by measuring the thickness of the front wall 103a at plurality of places including these two points and calculating the average of the front wall 103a.

The embodiment described herein includes the movement measuring unit 123 displaying the change in the thickness of the blood vessel wall and the change in the inner diameter of the blood vessel. These embodiments may be carried out by means of a variety of changes, such as measuring the change of the outer diameter of the blood vessel and that of the cross-section area of the blood vessel. Also, as mentioned in FIG. 9(a), if the heartbeat or the blood pressure is measured, the movement measuring unit 123 can measure the stiffness parameter or the blood vessel wall diameter direction average elasticity.

Many widely different embodiments of the invention may be configured without departing from the spirit and the scope of the present invention. It should be understood that the present invention is not limited to the specific embodiments described in the specification, except as defined in the appended claims.

The invention claimed is:

1. An ultrasound diagnostic apparatus comprising:
a transmitting and receiving unit configured to transmit an ultrasound wave to a target object in sequence and to receive the ultrasound wave as ultrasound data reflected from a certain region of the target object including a long axis direction blood vessel in sequence;
a first memory unit configured to store the received ultrasound data in sequence;
an image generation unit configured to generate an ultrasound image as a sectional image of the long axis direction blood vessel based on the received ultrasound data;
a display unit configured to display the ultrasound image generated by the image generation unit;
a region of interest setting unit configured to set a first region of interest on a vertical straight line at a right angle to the long axis direction blood vessel and a second region of interest on a wall of the blood vessel of the ultrasound image displayed in the display unit at a designated time, wherein the regions of interest are generated by ultrasound data stored in the first memory unit;
a tracing unit configured to trace movement of tissue in the target object corresponding to the first region of interest and the second region of interest from the designated time to sequentially following thereafter by a gradient method using a spatial brightness gradient; and
a second memory unit configured to store information of the movement of the tissue for a predetermined duration based on the movement of the tissue traced by the tracing unit.

2. The ultrasound diagnostic apparatus according to the claim 1, wherein the display unit is configured to display a traced result of the movement of the tissue on the vertical straight line or on a horizontal straight line normal to the vertical straight line based on the information of the movement of the tissue stored in the second memory unit.

3. The ultrasound diagnostic apparatus according to the claim 1, wherein the display unit is configured to display a traced result of a distance between at least two tissues on the vertical straight line based on the information of the movement of the tissue stored in the second memory unit.

4. The ultrasound diagnostic apparatus according to the claim 1, wherein the region of interest setting unit is configured to display points as indications of the first region of interest and the second region of interest on the display unit, and to set the first region of interest and the second region of interest including the points when the points are indicated.

5. The ultrasound diagnostic apparatus according to the claim 1, wherein the region of interest setting unit is configured to display a horizontal line in the long axis direction including the first region of interest on the display unit when the first region of interest is set on the vertical straight line, and to display the vertical line normal to the horizontal line including the first region of interest on the display unit when angle of the horizontal line is set.

6. The ultrasound diagnostic apparatus according to the claim 1, wherein the first region of interest includes a first inner wall of the blood vessel on the vertical straight line and the second region of interest includes a second inner wall of the blood vessel on the vertical straight line,
the display unit configured to display a traced result of an inner diameter of the blood vessel identified by the first region of interest and the second region of interest.

7. The ultrasound diagnostic apparatus according to the claim 2, wherein the first region of interest includes a first inner wall of the blood vessel on the vertical straight line and the second region of interest includes a second inner wall of the blood vessel on the vertical straight line,
the display unit configured to display a traced result of an inner diameter of the blood vessel identified by the first region of interest and the second region of interest.

8. The ultrasound diagnostic apparatus according to the claim 3, wherein the first region of interest includes a first inner wall of the blood vessel on the vertical straight line and the second region of interest includes a second inner wall of the blood vessel on the vertical straight line,
the display unit configured to display a traced result of an inner diameter of the blood vessel identified by the first region of interest and the second region of interest.

9. The ultrasound diagnostic apparatus according to the claim 4, wherein the first region of interest includes a first inner wall of the blood vessel on the vertical straight line and the second region of interest includes the other of inner a second inner wall of the blood vessel on the vertical straight line,
the display unit is configured to display a traced result of an inner diameter of the blood vessel identified by the first region of interest and the second region of interest.

10. The ultrasound diagnostic apparatus according to the claim 5, wherein the first region of interest includes a first inner wall of the blood vessel on the vertical straight line and the second region of interest includes a second inner wall of the blood vessel on the vertical straight line,
the display unit is configured to display a traced result of an inner diameter of the blood vessel identified by the first region of interest and the second region of interest.

11. The ultrasound diagnostic apparatus according to the claim 1, wherein the first region of interest includes a first outer wall of the blood vessel on the vertical straight line and the second region of interest includes a second outer wall of the blood vessel on the vertical straight line,
the display unit is configured to display a traced result of an outer diameter of the blood vessel identified by the first region of interest and the second region of interest.

12. The ultrasound diagnostic apparatus according to the claim 2, wherein the first region of interest includes a first outer wall of the blood vessel on the vertical straight line and the second region of interest includes a second outer wall of the blood vessel on the vertical straight line, the display unit is configured to display a traced result of an outer diameter of the blood vessel identified by the first region of interest and the second region of interest.

13. The ultrasound diagnostic apparatus according to the claim 3, wherein the first region of interest includes a first outer wall of the blood vessel on the vertical straight line and the second region of interest includes a second outer wall of the blood vessel on the vertical straight line, the display unit is configured to display a traced result of an outer diameter of the blood vessel identified by the first region of interest and the second region of interest.

14. The ultrasound diagnostic apparatus according to the claim 4, wherein the first region of interest includes a first outer wall of the blood vessel on the vertical straight line and the second region of interest includes a second outer wall of the blood vessel on the vertical straight line, the display unit is configured to display a traced result of an outer diameter of the blood vessel identified by the first region of interest and the second region of interest.

15. The ultrasound diagnostic apparatus according to the claim 5, wherein the first region of interest includes a first outer wall of the blood vessel on the vertical straight line and the second region of interest includes a second outer wall of the blood vessel on the vertical straight line, the display unit is configured to display a traced result of an outer diameter of the blood vessel identified by the first region of interest and the second region of interest.

16. The ultrasound diagnostic apparatus according to the claim 1, wherein the region of interest setting unit is configured to set a third region of interest and a fourth region of interest on the vertical straight line, the first region of interest includes a first inner wall of the blood vessel on the vertical straight line and the second region of interest includes a second inner wall of the blood vessel on the vertical straight line, the third region of interest includes a first outer wall of the blood vessel and the fourth region of interest includes a second outer wall of the blood vessel, the display unit is configured to display a change in duration of a thickness of the blood vessel identified by the first and second regions of interest and the third and fourth regions of interest.

17. The ultrasound diagnostic apparatus according to the claim 1, wherein the region of interest setting unit is configured to set a plurality of regions of interest corresponding to the first and second regions of interest, the plurality of regions of interest are at different positions than the first and second region of interests in the long axis direction.

18. The ultrasound diagnostic apparatus according to the claim 17, wherein the display unit is configured to display a traced result of an average distance based on the information of the movement of the tissue at the different positions in long axis direction stored in the second memory unit, the average distance between at least two tissues of the target object on the vertical straight line is calculated at a plurality different positions.

19. The ultrasound diagnostic apparatus according to the claim 4, wherein the region of interest setting unit is configured to set a new region of interest on a horizontal straight line, and the tracing unit is configured to trace the movement of the tissue in the target object corresponding to the new region of interest on the horizontal straight line, the display unit configured to display the points, the first region of interest, and the second region of interest when the first region of interest and the new region of interest are moved.

20. A method for tracing movement of tissue, the method comprising:

transmitting an ultrasound wave to a target object in sequence;

receiving the ultrasound wave as ultrasound data reflected from a certain region of the target object including a long axis direction blood vessel in sequence;

storing the received ultrasound data in sequence;

generating an ultrasound image as a sectional image of the long axis direction blood vessel based on the received ultrasound data;

displaying the ultrasound image;

setting a first region of interest on a vertical straight line at a right angle to the long axis direction blood vessel and a second region of interest on a wall of the blood vessel of the displayed ultrasound image at a designated time;

tracing movement of tissue in the target object corresponding to the first region of interest and the second region of interest from the designated time to sequentially following thereafter by a gradient method using a spatial brightness gradient; and storing information of the movement of the tissue for a predetermined duration based on the traced movement of the tissue.

* * * * *